United States Patent [19]

Barnett et al.

[11] Patent Number: 5,008,391

[45] Date of Patent: Apr. 16, 1991

[54] ENANTIOSELECTIVE SYNTHESIS OF ANTIFOLATES

[75] Inventors: Charles J. Barnett; Thomas M. Wilson, both of Indianapolis, Ind.

[73] Assignee: Eli Lilly and Company, Indianapolis, Ind.

[21] Appl. No.: 377,021

[22] Filed: Jul. 7, 1989

[51] Int. Cl.$^5$ .................. C07D 211/76; C07D 471/04; C07C 255/17; C07C 67/02
[52] U.S. Cl. .................................... 546/243; 546/287; 546/288; 546/291; 546/298; 544/279; 552/10; 552/11; 552/12; 558/398; 560/254
[58] Field of Search ............... 546/288, 287, 291, 298, 546/243

[56] References Cited

U.S. PATENT DOCUMENTS 4,684,653 8/1987 Taylor et al. ..................... 514/258
4,818,819 4/1989 Taylor et al. ..................... 544/279

FOREIGN PATENT DOCUMENTS 0248573 12/1987 European Pat. Off. ............... 471/4

OTHER PUBLICATIONS

G. M. Ramos Tombo, Tetrahedron Letters, vol. 27, No. 47, pp. 5707-5710, 1986.
G. M. Ramos Tombo, vol. 29, pp. 43-50, *Studies of Organic Chemistry*, Elsevier, Amsterdam, 1987.
Yi-Fong Wang and Charles J. Sih, Tetrahedron Letters, vol. 25, No. 44, pp. 4999-5002, 1984.
V. Kerscher and W. Kreiser, Tetrahedron Letters, vol. 28, No. 5, pp. 531-534, 1987.
Zbigniew J. Kaminski, Tetrahedron Letters, vol. 26, No. 24, pp. 2901-2904, 1985.

*Primary Examiner*—Anton H. Sutto
*Assistant Examiner*—J. Richter
*Attorney, Agent, or Firm*—Joseph A. Jones; Leroy Whitaker

[57] ABSTRACT

A process and intermediates for the enantioselective synthesis of 5,10-dideaza-5,6,7,8-tetrahydrofolic acid are disclosed.

4 Claims, No Drawings

ENANTIOSELECTIVE SYNTHESIS OF ANTIFOLATES

FIELD OF THE INVENTION

This invention belongs to the fields of pharmaceutical and synthetic organic chemistry, and provides processes and intermediates for the asymmetric synthesis of a series of complex antimetabolites of the antifolate type.

BACKGROUND OF THE INVENTION

Antimetabolites have been used for some years as chemotherapeutic agents in the treatment of cancer, as well as in the treatment of other conditions such as rheumatoid arthritis. One such drug, methotrexate, is now one of the most widely used anticancer drugs, and many other compounds in the folic acid family have been made, tested and discussed in the chemical and medical literature. The compounds have various activities at the enzymatic level; they inhibit enzymes such as dihydrofolate reductase and folate polyglutamate synthetase, to varying degrees and in varying combinations.

More recently, a series of derivatives of 5,10-dideaza-5,6,7,8-tetrahydrofolic acids has been disclosed and shown to be particularly useful anti-folate drugs. See, for example, U.S. Pat. No. 4,684,653, of E. C. Taylor et al., and European Patent Publication 0248573, of Taylor, Shih et al. Those compounds have two or more asymmetric centers. The asymmetric center at the 6-position (the junction of the tetrahydropyrimidine ring and the two-carbon bridge) is of particular interest and concern. It has been shown in the above EPO publication that the two stereoisomers wherein the 6-position center is in the R and the S configuration have different activities. Both forms are effective drugs, but their efficacies are different and one or the other would be preferred for various purposes. The patent publication shows a method for preparing and separating the two stereoisomers by use of a chiral salt. That procedure, however, is wasteful if only one of the stereoisomers is wanted in the circumstances. An enantioselective method of preparing either the 6R or the 6S stereoisomer of those compounds is provided by the present invention.

SUMMARY OF THE INVENTION

The present invention provides an enantioselective synthesis for preparing either the 6R or the 6S form of protected 5,10-dideaza-5,6,7,8-tetrahydrofolic acid derivatives of the formula

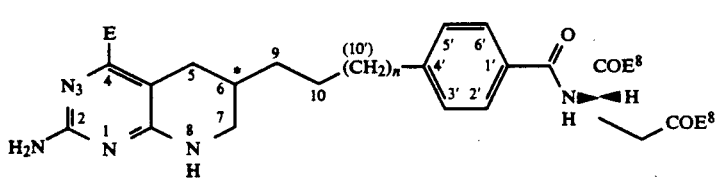

wherein the 6-position carbon, marked *, is in the R or the S configuration;
$E^8$ is a carboxy-protecting group;
n is 0 or 1;
and E is hydroxy or amino.

The invention also provides the substantially pure 6R and 6S isomers of a compound of the formula

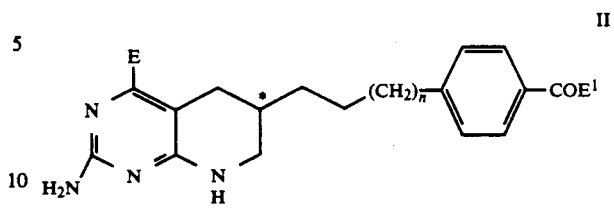

wherein $E^1$ is hydroxy or a carboxy-protecting group. The invention also provides piperidone intermediates of the formula

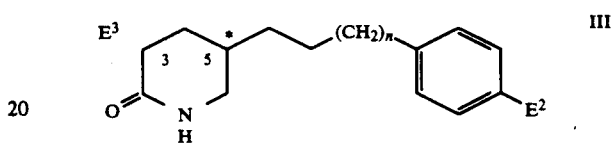

wherein $E^3$ is cyano or $C_1$-$C_3$ alkoxycarbonyl; $E^2$ is bromo, chloro, iodo, carboxy, $C_4$-$C_6$ tert-alkoxycarbonyl, cyano, $C_1$-$C_3$ alkylaminocarbonyl, di($C_1$-$C_3$ alkyl)aminocarbonyl or [(tetra or penta)methylene]aminocarbonyl; and the carbon marked * is in the R or S configuration.

Still a further group of valuable intermediates provided by the present invention are those of the formula

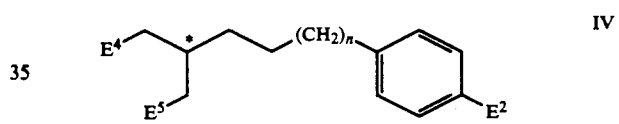

wherein either
(a) $E^4$ is hydroxy; $E^5$ is azido or $C_2$-$C_4$ alkanoyloxy; or
(b) $E^4$ is azido; $E^5$ is bis($C_1$-$C_3$ alkoxycarbonyl)methyl; or
(c) $E^4$ is azido; $E^5$ is ($C_1$-$C_3$ alkoxycarbonyl)(cyano)methyl;
and the carbon marked * is in the R or S configuration.

One of the valuable process steps provided by the present invention is a process for preparing a compound of the formula

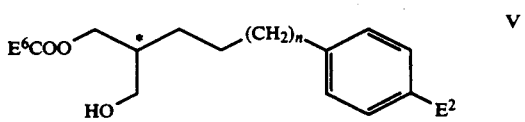

wherein $E^6$ is $C_1$-$C_3$ alkyl; and the carbon marked * is in the R configuration; comprising reacting a diol of the formula

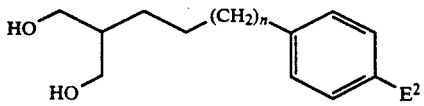

with an ester of the formula $$E^6-CO-O-CH_3 \quad\quad VII$$

in the presence of porcine pancreas lipase.

Finally, the invention provides a process for preparing a compound of formula I which comprises reacting an acid of formula II wherein $E^1$ is hydroxy, with a triazine of the formula

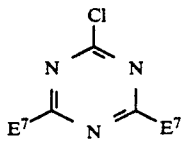

wherein the $E^7$ groups independently are chloro, methoxy or phenoxy; and then with a L-glutamate of the formula

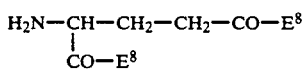

wherein the $E^8$ groups independently are carboxy-protecting groups, in the presence of N-methylmorpholine.

DETAILED DESCRIPTION OF THE INVENTION

Throughout the present document, all temperatures are expressed in degrees Celsius. All expressions of percentage, ratio and the like are in weight units, except in the case of mixtures of solvents, in which case units of volume are used.

In formula I above, the configuration of the L-glutamic acid residue is shown unambiguously. The glutamic acid residue in all compounds discussed in the present document is in the L-configuration, and that aspect of the compounds will not be described further, in order to simplify the nomenclature and structural formulae.

The point and virtue of the present invention is its ability to prepare the product of formula I in the form of a substantially pure stereoisomer, where the configuration of the 6-position (*) is predictable from the beginning of the process. Accordingly, each intermediate to those products is also in a predictable stereoisomeric form. The R,S nomenclature of Kahn, Prelog, and Ingold, Angew. Chem. Int. Ed. Engl., 1966 5 385, is used herein to describe the stereoisomers, because it unambiguously describes the absolute configuration of the asymmetric center. It will be understood, however, that the R,S nomenclature is determined according to rules which consider the nature of the exact compound being named. Accordingly, it is common to find that an intermediate wherein the asymmetric center is in the R configuration produces a product wherein the same center is in the S configuration, even if the asymmetric center is not directly involved in the reaction. Thus, if one is to prepare a product of formula I in the 6S configuration, one must begin by preparing an intermediate of formula V in the R configuration. The relationships are further explained in Scheme I.

The biologically most important compound of formula I, that wherein n is 0, and E and $E^8$ are hydroxy, has been referred to in the unprotected form as DDATHF. The stereoisomers of that compound have previously been designated isomer A and isomer B; see, for example, Taylor et al., *Chemistry and Biology of Pteridines*, Walter De Gruyter, Berlin, 1986, 61-64. Isomer B, the preferred isomer, is the 6R compound, and isomer A is the 6S compound.

It will be understood that a hydroxy E is in a tautomeric relationship with the keto form in these compounds. The hydroxy nomenclature is used throughout this document, and the reader will understand that both tautomeric forms are intended.

The products of formula I will be named as 5,10-dideaza-5,6,7,8-tetrahydrofolic acids and derivatives thereof. When E is amino, the compounds will be called 4-amino; and when n is 1, the term 10'-methylene will be used. When protecting groups are present on the carboxyl groups of the L-glutamic acid moiety, a group on the carboxyl adjacent to the asymmetric center will be called the α-group, and the group on the other carboxyl will be called the γ-group.

In the various structural formulae used in this document, the variable terms are described in a manner conventional in organic chemistry. For example, the term $C_1$-$C_3$ alkyl is used to include methyl, ethyl, propyl, and isopropyl. The terms $C_1$-$C_3$ alkoxycarbonyl and $C_4$-$C_6$ tert-alkoxycarbonyl include groups such as methoxycarbonyl, propoxycarbonyl, t-butoxycarbonyl, and 1,1-dimethylbutoxycarbonyl.

The terms $C_1$-$C_3$ alkylaminocarbonyl and di($C_1$-$C_3$ alkyl)aminocarbonyl include methylaminocarbonyl, diethylaminocarbonyl, methylisopropylaminocarbonyl, propylaminocarbonyl and the like.

The term carboxy-protecting group is used as it frequently is used in peptide chemistry, to refer to a group which will prevent a carboxyl group from participating in a reaction carried out on some other functional group of the molecule, but which can readily be removed from the carboxyl when it is desired to do so. Such groups are well discussed by Greene, *Protective Groups in Organic Synthesis*, Wiley, New York, 1981, pp. 152-92. It is there explained that carboxy-protecting groups include esters, amides and hydrazides, particularly such groups as phenacyloxy, trichloroethoxy, t-butoxy, triphenylmethoxy, trimethylsilyloxy, dimethylamino, silyl esters and the like.

The term $C_2$-$C_4$ alkanoyloxy includes acetoxy, propionyloxy, butyryloxy and isobutyryloxy.

While the full scope of the invention as described above is valuable, certain aspects of the invention are particularly valuable and are preferred. The preferred aspects are described in the following subparagraphs. It will be understood that further, more highly preferred aspects of the invention are described by combining limitations set out below.

In the compounds of formulae II, the following are preferred limitations.

A. E is hydroxy;
B. The configuration at the 6-position carbon is R;
C. n is 0;
D. $E^1$ is hydrogen;
E. $E^1$ is a carboxy-protecting group.

In the compounds of formula III, preferred limitations are as follows:

A. $E^3$ is $C_1$–$C_3$ alkoxycarbonyl;
B. $E^3$ is cyano;
C. The configuration at the 5-position carbon is R;
D. n is 0;
E. $E^2$ is bromo, chloro or iodo;
F. $E^2$ is carboxy, alkoxycarbonyl or aminocarbonyl;
G. $E^2$ is cyano.

D. The process is carried out in an amide solvent.

The chief significance of the present invention lies in its ability to prepare the valuable anticancer drugs of formula I in a specific absolute configuration. According to the modern practice, the compounds are specified according to the R and S nomenclature, which is determined in a different manner for the various intermediate compounds used in the present invention. Scheme I is provided to illustrate the sequence of events.

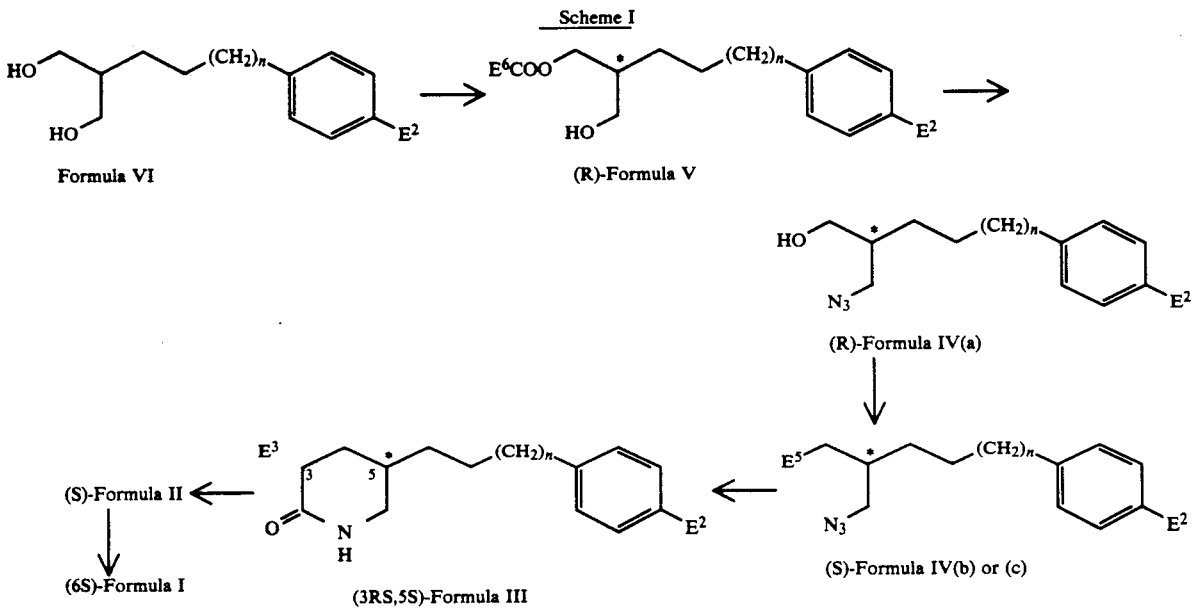

In the compounds of formula IV, the following are preferred limitations:

A. $E^4$ is hydroxy;
B. $E^4$ is azido;
C. $E^5$ is alkanoyloxy;
D. $E^5$ is acetoxy;
E. $E^5$ is bis(alkoxycarbonyl)methyl;
F. $E^5$ is bis(ethoxycarbonyl)methyl;
G. $E^5$ is (ethoxycarbonyl)(cyano)methyl;
H. $E^5$ is (alkoxycarbonyl)(cyano)methyl;
I. The configuration at the asymmetric center is S, in the case of formula IV(a), or is R, in the case of formulae IV(b) or (c);
J. n is 0;
K. $E^2$ is bromo, chloro, or iodo;
L. $E^2$ is carboxy, alkoxycarbonyl or aminocarbonyl;
M. $E^2$ is cyano.

In the process wherein the compound of formula VI is acylated to form the chiral compound of formula V, it is preferred to carry out the process without a solvent other than the ester, of which methyl acetate is preferred. The preferred definitions of $E^2$ in the compounds of formulae V and VI are the same as in formula IV.

In the process for preparing the compounds of formula I, the preferred definitions of E and n and the preferred configuration at the 6-position are as described above in the description of the formula I and II compounds. Further preferred limitations of the process are as follows.

A. $E^8$ is a $C_1$–$C_4$ alkoxy group;
B. $E^8$ is a $C_1$–$C_4$ alkoxy, benzyloxy or aryloxy group;
C. The product of the reaction with the triazine is not isolated or purified;

In the first step, the diol of formula VI is enantioselectively acylated with the aid of porcine pancreas lipase to form the chirally-specified intermediate of formula V, which is in the R configuration by virtue of the enzyme's specificity.

The intermediate of formula V is then transformed by processes to be described later to the R-configuration intermediate of formula IV(a). That intermediate is then transformed to the S-configuration intermediate of formula IV(b or c) wherein $E^5$ is bis(alkoxycarbonyl)-methyl, or is (alkoxycarbonyl)(cyano)methyl, depending on the desired E group in the final product. That intermediate is then cyclized to the piperidone of formula III, which is also in the S-configuration. It is cyclized again to form the S-configuration compound of formula II. Finally, that compound is reacted with the glutamic acid derivative to form the 6S-configuration drug of formula I.

If the objective is the 6R-configuration compound of formula I, then a transformation is effected as shown in Scheme II. The hydroxy group of the R-configuration intermediate of formula V is protected, and the acyl group is removed and replaced with azido to prepare the S-configuration intermediate of formula IV(a). The process according to Scheme I proceeds from there in the same manner as just discussed, to prepare the 6R-configuration compounds of formulae II and I.

Alternatively, the S intermediate of formula IV(a) can be obtained by bis-acylating the diol of formula VI, and mono-deacylating the resulting compound by hydrolysis in the presence of porcine pancreatic lipase. The hydrolysis is best carried out in an aqueous buffer at pH 7. The desired mono-acyl compound of formula IV in the S configuration is obtained, but the yield and enantiomeric purity of that intermediate is inferior to the results of Scheme II.

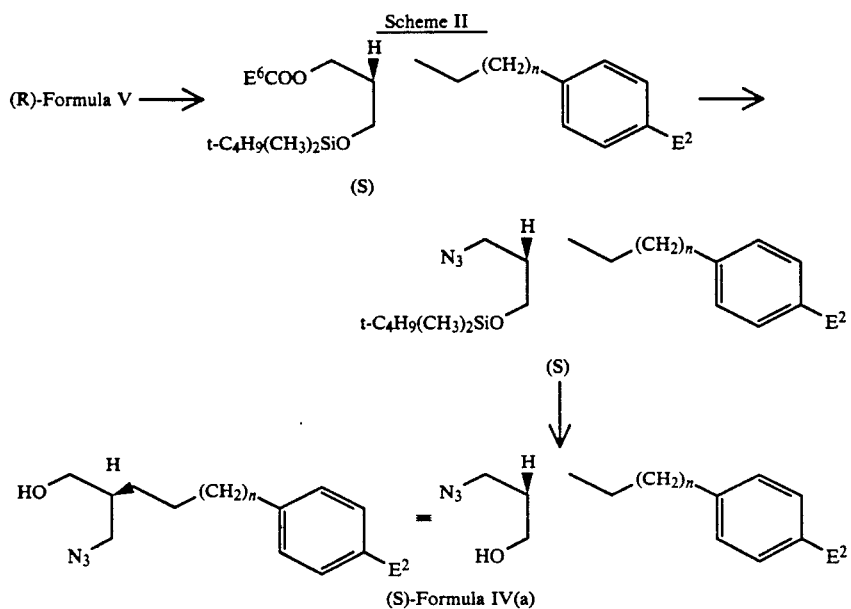

The starting compound of formula VI is prepared by conventional organic chemical methods. In the first step of the process outlined above, porcine pancreas lipase is used as a catalyst to prepare the mono ester of formula V in chirally determinate form. The specificity of the enzyme directs the esterification so that the product is in the R-configuration.

Porcine pancreas lipase can be purchased from sources such as Sigma Chemical Co. It is preferred to use it in immobilized form. For example, the lipase may be immobilized on a support such as diatomaceous earth commonly used for filter aid. The lipase need not be purified prior to immobilization. It is preferred to carry out the enzymatic esterification without a solvent other than an excess amount of the reactant ester, such as methyl acetate. It is possible, however, to use an organic solvent which is inert to the reaction conditions, such as an aromatic solvent or a halogenated solvent, if the circumstances call for it. The reaction is preferably carried out at a temperature in the ambient range, such as from about 0° to about 50°. When carried out in a batchwise manner, the reaction proceeds in a few hours; it could well be advantageous to carry the process out in a continuous manner, by passing a reaction mixture through a fixed bed of the immobilized enzyme. Esterification yields in the range of 90 percent have been obtained, and the product acetate is usually 90–95 percent pure R-configuration product.

As explained, the enzymatic esterification provides the R-configuration compound of formula V, which leads to the 6S-configuration product of formula I. When the preferred 6R-configuration product of formula I is to be prepared, the R-configuration intermediate of formula V is converted according to Scheme II to the S-configuration intermediate of formula IV(a). In this sequence of steps, the hydroxy group of the compound of formula V, prepared by the enzymatic esterification step, is protected with a conventional hydroxy-protecting group, as discussed in Greene, cited above. The preferred hydroxy-protecting group for this purpose is a silyl group, preferably t-butyldimethylsilyl. The silyl group is readily put in place by reaction with t-butyldimethylsilyl chloride at ambient temperature in an inert solvent such as a halogenated alkane, in the presence of a reaction initiator such as imidazole.

Then the ester group ($E^6OCO$) of the compound is cleaved with base to release the hydroxy group which had originally been acylated in the enzymatic step, and that hydroxy group is replaced with azide. It is best to put a leaving group, such as toluenesulfonyl or methanesulfonyl, on the hydroxy group, as by reaction with the chloride of the sulfonyl compound in the presence of a base such as triethylamine. Then reaction with an azide, most simply, sodium azide, removes the sulfonate group and replaces it with the desired azide group.

Finally, the silyl protecting group is removed by acid hydrolysis, as with acetic acid, to provide the desired S-configuration intermediate of formula IV(a) as shown in Scheme II.

In the second step of Scheme I, when the R-configuration compound of formula V is to be carried on through the process leading to the 6S-configuration drug of formula I, its hydroxy group is exchanged for an azide as described above, by adding an activating group to the hydroxy and reacting with, for example, sodium azide. The ester group is then hydrolyzed under, for example, acid conditions, as with a mineral acid in an alcohol or aqueous alcohol medium, to obtain the R-configuration compound of formula IV(a).

The hydroxy group of that compound is then removed, and replaced by the bis(alkoxycarbonyl)methyl or (alkoxycarbonyl)(cyano)methyl group of a compound of formula IV(b) or (c). That process step is accomplished by adding an activating group to the hydroxy, as by reaction of toluenesulfonyl chloride or methanesulfonyl chloride in the presence of a base such as triethylamine. Reaction of the sulfonate with an alkali metal enolate of a malonic diester, or an alkyl 1-cyanoacetate, preferably in the presence of an iodide salt, provides the desired S-configuration intermediate of formula IV(b) or (c), respectively.

That intermediate is then cyclized to form the S-configuration compound of formula III, by reaction with a trialkyl or triaryl phosphine in a water-containing reaction medium. Aqueous tetrahydrofuran, for example is a satisfactory reaction medium. The reaction is exothermic and releases a stoichiometric equivalent of nitrogen, and it must therefore be carefully controlled. When the compound of formula IV(b) or (c) has a bis(alkoxycarbonyl)methyl group, $E^3$ in the intermediate of formula III is a corresponding alkoxycarbonyl group; $E^3$ is cyano when $E^5$ is a (alkoxycarbonyl)(cyano)methyl group.

Before the compound of formula III is cyclized to prepare the S-configuration compound of formula II, the oxo group of the piperidone is converted to an alkoxy by reaction with a trialkyloxonium tetrafluoroborate. The reaction proceeds well at elevated temperature, such as the reflux temperature of the reaction mixture.

The resulting 2-methoxytetrahydropyridine is then cyclized with guanidine to prepare the compound of formula II, or a compound related to formula II in which the terminal carboxy group has not yet been formed. The reaction with guanidine proceeds in short periods of time at an elevated temperature in the range of 50–100°. Guanidine may be supplied as a salt, which must be converted to the free base by neutralization with base.

The carboxy group on the phenyl ring of that compound is then formed, if the group $E^2$ in the intermediates up to this point is not carboxy. For example, if $E^2$ is a halogen atom, it is most conveniently replaced with cyano by reaction with a cyano salt such as copper (1) cyanide in the presence of N-methylpyrrolidine. The nitrile group is then hydrolyzed as with a strong mineral acid, to obtain the desired compound of formula II. If $E^2$ in the intermediate is an alkoxycarbonyl or aminocarbonyl group, it is simply hydrolyzed with base to obtain the carboxy compound.

Finally, the anticancer drug of formula I is prepared by reacting the intermediate of formula II with an appropriate derivative of glutamic acid. Both of the reactants may conveniently be in the form of acid addition salts when added to the reaction mixture. The glutamic acid should be in the form of a protected derivative of formula IX, wherein $E^8$, most preferably, is an alkoxy group, particularly an ethyl or t-butyl group. The reaction with the glutamate is carried out by an intermediate reaction with the triazine of formula VIII, preferably that wherein $E^7$ is methoxy, in the presence of N-methylmorpholine. When the reaction is carried out in this manner, substantially no racemization of the L-glutamate stereocenter is observed. In a final step, the protecting groups on the glutamic acid moiety may be removed by conventional means, as by hydrolysis.

The following preparations and examples further explain the synthesis of the various intermediates and products of the present invention, as well as the novel process steps provided by the invention.

In the following procedures, products were often analyzed by high performance liquid chromatography (HPLC), which was carried out on a system consisting of a solvent delivery system, a spectrophotomoter and an integrator. Three methods were used in HPLC, as follows:

(Method A) Waters u-Bondapak 25 cm, $C_{18}$ column (Waters Div., Millipore Corp., Milford, Mass. 01757); 3:2 acetonitrile:water mobile phase at a flow rate of 2 ml/min; ultraviolet (UV) detector set at 254 nm.

(Method B) BakerBond Chiralcel-OD 25 cm column (J. T. Baker, Inc., Phillipsburg, N.J. 08865); 2:2:1 hexane:ethanol:n-propanol mobile phase at a flow rate of 1 ml/min; UV detector set at 280 nm.

(Method C) Waters u-Bondapak 25 cm $C_{18}$ column; 27:73 acetonitrile:water mobile phase with 0.025% trifluoroacetic acid at a flow rate of 2 ml/min; UV detector set at 254 nm.

All $^1$H and $^{13}$C nuclear magnetic resonance (NMR) spectra were obtained on a NMR instrument at 300 MHz and 75.5 MHz respectively. The solvent used in NMR determinations was CDCl$_3$. All NMR peaks are reported in ppm relative to chloroform at 7.26 ppm (proton) and 77.06 ppm (carbon).

EXAMPLE 1

(R)-4-(4-bromophenyl)-2-(hydroxymethyl)butyl acetate

An immobilized preparation of porcine pancreatic lipase (PPL) was prepared by suspending 16 g of PPL in 160 ml of 18 mM trisodium phosphate at pH 12, centrifuging the suspension for one hour at 5000 rpm, cooling the centrifugate to 0°, and stirring into it 45 g of finely powdered diatomaceous earth. To that suspension was slowly added 270 ml of 0° acetone, and the immobilized enzyme was removed by filtration and dried under vacuum to obtain 50.2 g of solids containing 5.2 g of enzyme. The PPL was Sigma (Sigma Chemical Co., Box 14508, St. Louis, Mo. 63178); type II, no. 3126, containing 36 units/mg of protein or 13.3 unit/mg of solid.

To a solution of 4.6 g of 4-(4-bromophenyl)-2(hydroxymethyl)butanol in 300 ml of methyl acetate was added 33.1 g of the above PPL preparation. The mixture was stirred while the progress of the reaction was monitored by HPLC method A. When the consumption of diol was complete, the mixture was immediately filtered and the filtrate was concentrated to an oil under vacuum. The oil was purified by flash chromatography on 200 g of silica with 3:1 ethyl acetate: hexane to obtain 4.82 g of the desired product as an oil. The 1-naphthyl carbamate derivative of a small portion of the product was prepared and analyzed by HPLC method B to determine that the product was 99% R and 1% S; the R isomer eluted at 9.4 minutes, and the S isomer at 12.6 minutes.

TLC(3:1 ethyl acetate:hexane, silica)R$_f$0.45;
$^1$H NMR δ 7.39 (d, J=8.3 Hz, 2H), 7.05 (d, J =8.3 Hz, 2H), 4.21 (dd, J=4.5, 11.3 Hz, 1H), 4.13 (d, J=6.3, 11.3 Hz, 1H), 3.62 (dd, J=4.6, 11.2 Hz, 1H), 3.56 (dd, J=5.1, 11.2 Hz, 1H), 2.64 (t, J=8.0 Hz, 2H), 2.07 (s, 3H), 1.94 (s, 1H), 1.83 (m, 1H), 1.64 (m, 2H); $^{13}$C NMR δ 171.25, 140.78, 131.27, 129.91, 119.44, 64.30, 62.21, 39.79, 32.39, 29.36, 20.62; IR (CHCl$_3$) 3635, 2940, 1727, 1485, 1360, 1246, 1038 cm−$^1$; MS (EI), m/z 302 (2), 300 (2), 184 (65), 182 (67), 171 (24), 169 (28), 90 (23), 43 (100); UV (EtOH) 221 nm (ε=11000), 268 nm (ε=345), 276 nm (ε=260).

Analysis Calculated for C$_{13}$H$_{17}$BrO$_3$: C, 51.84; H, 5.67
Found: C, 51.86; H, 5.89.

EXAMPLE 2

(R)-2-azidomethyl-4-(4-bromophenyl)butanol

A solution of 2.5 g of the product of Example 1 and 0.84 g of triethylamine in 10 ml of dichloromethane was cooled to 0°. To the solution was added dropwise a solution of 0.95 g of methanesulfonyl chloride in 5 ml of dichloromethane. The mixture was stirred at 0° for 45 minutes, and was then allowed to warm to ambient temperature over a period of 20 minutes. Then 15 ml of 1M hydrochloric acid was added, the phases were separated, and the organic phase was washed with 15 ml of saturated sodium bicarbonate, dried over sodium sulfate and concentrated under vacuum. The residue was purified on 150 g of silica gel by flash chromatography, eluting with 1:1 hexane:ethyl acetate, to obtain 3.0 g of (S)-4-(4-bromophenyl)-2-(methanesulfonyloxymethyl)-butyl acetate as an oil.

$[\alpha]_{589}+2.35°$, $[\alpha]_{365}+7.69°$ (c 0.8, $CHCl_3$); HPLC Method A $t_R$: 4.3 min; TLC (1:1 ethyl acetate:hexane, silica) $R_f$ 0.46; $^1H$ NMR δ 7.38 (d, J=8.3 Hz, 2H), 7.03 (d, J=8.3 Hz, 2H), 4.21 (d, J=5.2 Hz, 2H), 4.14 (dd, J=4.7, 11.3 Hz, 1H), 4.06 (dd, J=6.7, 11.3 Hz, 1H), 2.97 (s, 3H), 2.63 (t, J=8.0 Hz, 2H), 2.06 (m, 1H), 2 04 (s, 3H), 1.63 (m, 2H); $^{13}C$ NMR δ 170.54, 139.99, 131.48, 129.97, 119.71, 68.79, 62.95, 37.20, 32.06, 29.10, 20.62; IR ($CHCl_3$) 3030, 2940, 1738, 1489, 1355, 1330, 1233, 940 $cm^{-1}$; MS (EI), m/z 380 (2), 378 (3), 184 (85), 182 (87), 171 (29), 169 (33), 143 (24), 130 (10), 128 (15), 90 (37), 79 (23), 77 (17), 43 (100); UV (EtOH) 220 nm (ε=11500), 268 nm (ε=311), 276 nm (ε=237).

Analysis Calculated for $C_{14}H_{19}BrO_5S$: C, 44.34; H, 5.05

Found: C, 44.42; H, 5.21.

A 2.8 g portion of the above intermediate and 0.51 g of sodium azide were dissolved in 25 ml of dimethylformamide and the solution was heated at 75° for four hours. Then 25 ml of water and 25 ml of ethyl acetate were added, and the organic phase was separated, washed with brine, dried over sodium sulfate and concentrated under vacuum. The residue was purified by flash chromatography on 120 g of silica gel, eluting with 2:3 ethyl acetate:hexane, to obtain 2.0 g of (R)-2-azidomethyl-4-(4-bromophenyl)butyl acetate as an oil.

$[\alpha]_{589}+3.71°$, $[\alpha]_{365}+12.85°$ (c 0.8, $CHCl_3$); HPLC Method A $t_R$:7.8 min.; TLC (2:3 ethyl acetate:hexane, silica) $R_f$ 0.60; $^1H$ NMR δ 7.37 (d, J=8.3 Hz, 2H), 7.03 d, J=8.3 Hz, 2H), 4.10 (dd, J=4.8, 11.3 Hz, 1H), 4.03 (d, J=6.6, 11.2 Hz, 1H), 3.36 (d, J=5.7 Hz, 2H), 2.60 (t, J=8.0 Hz, 2H), 2 05 (s, 3H), 1.89 (m, 1H), 1.65 (m, 2H); $^{13}C$ NMR δ 170.6, 140.23, 131.39, 129.89, 119.66, 64.06, 52.35, 37.36, 32.17, 30.23, 20.64; IR ($CHCl_3$) 2940, 2103, 1736, 1489, 1450, 1380, 1238, 1035 $cm^{-1}$; MS (EI), m/z 198 (30), 197 (37), 196 (33), 195 (36), 184 (25), 182 (27), 171 (52), 169 (54), 118 (32), 90 (56), 56 (42), 43 (100); UV (EtOH) 221 nm (ε=11000), 268 nm (ε=297), 276 nm (ε=218).

Analysis Calculated for $C_{13}H_{16}BrN_3O_2$:
C, 47.86; H, 4.94; N, 12.88
Found: C, 48.10; H, 5.03; N, 12.60.

A 1.9 g portion of the above intermediate was dissolved in 10 ml of 2.7M hydrochloric acid in dry ethanol, and the solution was stirred at ambient temperature for three hours and concentrated under vacuum. The residue was treated again in the same way with ethanolic hydrochloric acid. The residue was then purified by flash chromatography on 120 g of silica gel, eluting with 1:1 ethyl acetate:hexane, to obtain 1.4 g of (R)-2-azidomethyl-4-(4-bromophenyl)butanol.

$[\alpha]_{589}+1°$, $[\alpha]_{365}+4.5°$ (c 0.8, $CHCl_3$); HPLC Method A $t_R$:4.0 min.; TLC (1:1 ethyl acetate:hexane, silica) $R_f$ 0.40; $^1H$ NMR δ 7.39 (d, J=8.3 Hz, 2H), 7.04 (d, J=8.3 Hz, 2H), 3.66 (dd, J=4.4, 10.8 Hz, 1H), 3.59 (dd, J=6.1, 10.8 Hz, 1H), 3.45 (dd, J=5.1, 12.2 Hz, 1H), 3.41 (dd, J=6.0, 12.2 Hz, 1H), 2.61 (t, J=7.9 Hz, 2H), 2.08 (s, 1H), 1.76 (m, 2H); $^{13}C$ NMR δ 140.61, 131.43, 129.95, 119.64, 63.09, 52.68, 40.09, 32.46, 30.10; IR ($CHCl_3$) 3625, 2930, 2102, 1480 $cm^{-1}$; MS (EI), m/z 256 (18), 254 (20), 226 (25), 224 (21), 199 (40), 198 (72), 197 (52), 196 (69), 184 (21), 182 (19), 171 (98), 169 (100), 129 (30), 118 (64), 90 (84); UV (EtOH) 221 nm (ε=11300), 268 nm (ε=313), 276 nm (ε=235).

Analysis Calculated for $C_{11}H_{14}BrN_3O$:
C, 46.50; H, 4.97; N, 14.79
Found: C, 46.48; H, 4.72; N, 14.90.

EXAMPLE 3

(S)-[2-azidomethyl-4-(4-bromophenyl)butyl]propanedioic acid, diethyl ester

A 1.2 g portion of the product of Example 2 was dissolved in 5 ml of dichloromethane with 0.49 g of methanesulfonyl chloride and the solution was cooled to 0°. To it was added dropwise a solution of 0.43 g of triethylamine in 3 ml of dichloromethane. The mixture was then allowed to stir for two hours while it warmed to ambient temperature. Eight ml of 1M hydrochloric acid was then added, and the organic phase was separated, washed with 8 ml of saturated sodium bicarbonate solution, dried with sodium sulfate, and concentrated under vacuum. The residue was purified by flash chromatography on silica gel, eluting with 2:3 ethyl acetate:hexane to obtain 1.5 g of (R)-2-azidomethyl-4-(4-bromophenyl)butanol methanesulfonate.

$[\alpha]_{589}+1.72°$, $[\alpha]_{365}+3.68°$ (c 0.8, $CHCl_3$); HPLC Method A $t_R$: 5.72 min.; TLC (2:3 ethyl acetate:hexane, silica) $R_f$ 0.49; $^1H$ NMR δ 7.39 (d, J=8.3 Hz, 2H), 7.05 (d, J=8.3 Hz, 2H), 4.20 (m, 2H), 3.46 (dd, J=5.1, 12.9 Hz, 1H), 3.40 (dd, J=6.0, 12.9 Hz, 2H), 3.01 (s, 3H), 2.62 (t, J=7.9 Hz, 2H), 1.96 (m, 1H), 1.67 (m, 2H); $^{13}C$ NMR δ 139.85, 131.52, 129.95, 119.84, 69.06, 51.42, 37.77, 37.16, 32.06, 29.04; IR ($CHCl_3$) 2939, 2104, 1489, 1362, 1176, 971 $cm^{-1}$; MS (EI), m/z 334 (16), 332 (14), 226 (14), 224 (19) 199 (60), 198 (70), 197 (66), 196 (74), 171 (100), 169 (90), 129 (43), 90 (83), 79 (43), 55 (37); UV (EtOH) 220 nm (ε=12700); 264 nm (ε=959), 276 nm (ε=748).

Analysis Calculated for $C_{12}H_{16}BrN_3O_3S$:
C, 39.79; H, 4.45; N, 11.60
Found: C, 40.02; H, 4.53; N, 11.73.

A 0.7 g portion of diethyl malonate in 5 ml of dry tetrahydrofuran was added to a rapidly stirred suspension of 96 mg of oil free sodium hydride in 10 ml of dry tetrahydrofuran. When the evolution of gas had stopped, a solution of 1.3 g of the intermediate prepared above in 10 ml of dry tetrahydrofuran and 110 mg of sodium iodide were added to the reaction mixture and it was stirred under reflux for 18 hours. The mixture was then cooled, and was partitioned by the addition of 20 ml of ethyl acetate and 15 ml of saturated sodium chloride solution. The organic phase was separated, dried with sodium sulfate and concentrated under vacuum, and the residue was purified by flash chromatography on 75 g of silica gel, eluting with 2:3 ethyl acetate:hexane, to obtain 0.75 g of the desired product as an oil.

$[\alpha]_{589}+2.73°$ (c 0.8, $CHCl_3$), HPLC Method A $t_R$: 14.0 min.; TLC (2:3 ethyl acetate:hexane, silica) $R_f$ 0.41; $^1H$ NMR δ 7.37 (d, J=8.3 Hz, 2H), 7.03 (d, J=8.3 Hz, 2H), 4.16 (m, 4H), 3.42 (t, J=7.6 Hz, 1H), 3.33 (d, J=4.7 Hz, 2H), 2.58 (t, J=7.6 Hz, 2H), 1.95 (m, 2H), 1.67 (m, 3H), 1.24 (m, 6H); $^{13}C$ NMR δ 168.98, 140.52, 131.45, 129.95, 119.62, 61.35, 54.65, 49.78, 35.87, 33.40, 32.12, 31.04, 13.91; IR ($CHCl_3$) 2985, 2926, 2102, 1744, 1726, 1489, 1232, 1178, 1154 $cm^{-1}$; MS (EI), m/z 326 (12), 324(12), 199 (67), 198 (48), 197 (69) 196 (51), 171 (100), 169 (89), 118 (48), 90 (61), 56 (86); UV (EtOH) 221 nm ($\epsilon=12300$), 268 nm ($\epsilon=419$), 276 nm ($\epsilon=308$).

Analysis Calculated for $C_{18}H_{24}BrN_3O_4$:
C, 50.71; H, 5.67; N, 9.86
Found: C, 50.50; H, 5.47; N, 9.69.

EXAMPLE 4

(3RS,5S)-3-ethoxycarbonyl-5-[2-(4-bromophenyl)ethyl]-2-piperidone

To a solution of 11.3 g of the compound of Example 3 and 0.5 g of water in 30 ml of tetrahydrofuran was added dropwise 5.6 g of tributyl phosphine. A vigorous exothermic reaction occurred, with the evolution of nitrogen, and the mixture was stirred for 25 minutes. The mixture was then dried with sodium sulfate and concentrated under vacuum. The residue was purified by flash chromatography on 1.4 kg of silica gel, eluting first with 6 l of 19:1 dichloromethane: ethanol followed by 4 l of 9:1 dichloromethane:ethanol to obtain 6.8 g of yellow oil, which could be crystallized from hexane as a 2:3 mixture of diastereomers at the 3-position.

mp 101-104, 108-113 (mixture of diastereomers); HPLC Method A $t_R$: 3.2 min., 3.4 min.; TLC (19:1 $CH_2Cl_2$:ethanol, silica) $R_f$ 0.28, 0.34; $^1H$ NMR $\delta$ 7.49 (s, 1H), 7.45 (s, 1H), 7.36 (d, J=8.4 Hz, 2H), 7.35 (d, J=8.4 Hz, 2H), 7.00 (d, J=8.4 Hz, 4H), 4.19 (q, J=7.1 Hz, 2H), 4.15 (q, J=7.8 Hz, 2H), 3.34 (m, 2H), 2.98 (t, J=11.0 Hz, 1H), 2.94 (t, J=13.0 Hz, 1H), 2.55 (m, 2H), 2.15 (m, 1H), 1.93 (m, 2H), 1.59 (m, 2H), 1.25 (t, J=7.1 Hz, 3H), 1.22 (t, J=7.8 Hz, 3H),; $^{13}C$ NMR $\delta$ 170.38, 168.24, 167.94, 140.28, 140.22, 131.45, 131.40, 129.87, 129.83, 119.70, 119.66, 61.30, 61.13, 48.80, 47.26, 47.07, 46.94, 34.74, 34.14, 32.37, 32.26, 31.12, 31.03, 30.26, 29.41, 13.98; IR (KBr) 3200, 2932, 1743, 1734, 1673, 1487, 1372, 1330, 1261, 1173, 1152, 1010 cm$^{-1}$; MS (EI), m/z 355 (53), 353 (51), 171 (100), 169 (95), 124 (35), 115 (29), 99 (36), 98 (47), 97 (52), 96 (41), 90 (71), 89 (43), 55 (89); UV (EtOH) 220 nm ($\epsilon=12200$), 268 nm ($\epsilon=331$), 276 nm ($\epsilon=247$).

Analysis Calculated for $C_{16}H_{19}BrNO_3$:
C, 54.40; H, 5.42; N, 3.97
Found C, 54.16; H, 5.62; N, 3.92.

PREPARATION 1

(6S)-2-amino-4-hydroxy-6-[2-(4-bromophenyl)ethyl]-5,6,7,8-tetrahydropyrido[2,3-d]pyrimidine A solution of 515 mg of the product of Example 4 and 236 mg of trimethyloxonium tetrafluoroborate in 3 ml of chloroform was heated under reflux for four hours. The mixture was then cooled to ambient temperature, and 2 ml of 50% aqueous potassium carbonate was added. Then 10 ml of water and 10 ml of chloroform were added, and the organic phase, containing solids, was dried with magnesium sulfate. The solids were removed by filtration, and the supernatant was concentrated under vacuum. The residue was purified by spinning plate thin layer chromatography on a 2 mm silica gel plate, with 1:1 ethyl acetate:hexane, to obtain 286 mg of (3RS,5S)-2-methoxy-3-ethoxycarbonyl-5-[2-(4-bromophenyl)ethyl]-3,4,5,6-tetrahydropyridine, as a 1:1 mixture of the 3-position diastereomers.

TLC (1:1 ethyl acetate:hexane, silica) $R_f$ 0.41; $^1H$ NMR $\delta$ 7.34 (d, J=8.4 Hz, 2H), 7.32 (d, J=8.4 Hz, 2H), 6.99 (d, J=8.4 Hz, 2H), 6.98 (d, J=8.4 Hz, 2H), 4.14 (q, J=7.0 Hz, 2H), 4.11 (q, J=7.5 Hz, 2H), 3.66 (m 1H), 3.61 (s, 3H),33.58 (s, 3H), 3.20 (m, 1H), 3.05 (m, 1H), 2.56 (m, 2H), 2.08 (m, 1H), 1.60 (m, 3H), 1.24 (t, J=7.5 Hz, 3H), 1.18 (t, J=7.0 Hz, 3H); $^{13}C$ NMR $\delta$ 171.27, 171.08, 158.56, 158.47, 140.87, 140.78, 131.40, 131.35, 129.96, 129.84, 119.57, 119.53, 61.05, 60.95, 52.62, 52.51, 52.38, 52.34, 44.95, 42.52, 34.99, 34.62, 32.49, 32.36, 31.91, 31.83, 31.16, 30.25, 29.19, 14.02; IR (CHCl$_3$) 2943, 1731, 1684, 1488, 1328, 1265, 1241, 1235, 1232, 1177, 1161, 1012 cm$^{-1}$; MS (EI), m/z 369 (19), 367 (16), 186 (11), 185 (100), 184 (15), 171 (31), 169 (36), 124 (26), 115 (21), 113 (37), 112 (37), 85 (27).

A 1.9 g portion of guanidine hydrochloride and 1.36 g of sodium ethoxide were dissolved in 20 ml of dry ethanol and heated to 70° for 20 minutes. The mixture was then cooled and filtered, and the supernatant was added to 1.8 g of the above intermediate. The solution was stirred briefly and then concentrated under vacuum to a slurry. The flask was then purged with dry nitrogen, and was heated to 70° for one hour. The mixture was then cooled to ambient temperature, 20 ml of methanol was added and a precipitate quickly formed after brief agitation. The mixture was then cooled to 0° overnight, and was filtered and the solids were washed with diethyl ether to obtain 1.4 g of the desired product.

EXAMPLE 5

(6S)-2-amino-4-hydroxy-6-[2-(4-carboxyphenyl)ethyl]-5,6,7,8-tetrahydropyrido[2,3-d]pyrimidine A 750 mg portion of the product of Preparation 1, 365 mg of copper cyanide and 6 ml of 1-methyl-2-pyrrolidinone were combined, blanketed with nitrogen, and heated at reflux for four hours. The mixture was then cooled to ambient temperature and concentrated under vacuum. To the slurry was added 6 ml of 6M hydrochloric acid and the mixture was stirred for 10 minutes. The mixture was then filtered, and the solids were washed with methanol and then with diethyl ether, and air dried to obtain 613 mg of (6S)-2-amino-4hydroxy-6-[2-(4-cyanophenyl)ethyl]-5,6,7,8-tetrahydropyrido [2,3-d]pyrimidine, 95% pure by HPLC method A.

A 52 mg portion of the above intermediate was combined with 2 ml of 6M hydrochloric acid and was heated under reflux for 70 hours. The mixture was then cooled and filtered and the solids were washed with 2 ml of water, 2 ml of methanol, and 5 ml of diethyl ether, and were air dried to obtain 35.5 mg of the desired product as the hydrochloride salt.

EXAMPLE 6

(6S)-5,10-dideaza-5,6,7,8-tetrahydrofolic acid

To a suspension of 20 mg of the product of Example 5 and 12 mg of N-methylmorpholine in 300 µl of dimethylformamide was added 10 mg of 2-chloro-4,6-dimethoxy-1,3,5-triazine. The mixture was stirred for 20 minutes, and then 6 mg of additional N-methylmorpholine and 15 mg of L-glutamic acid diethyl ester hydrochloride were added. The mixture was stirred for 20 minutes at ambient temperature, and was then filtered and concentrated under vacuum. The residue was hydrolyzed with 1 ml of 1N sodium hydroxide to saponify the product and produce the desired product, which was found to be identical with an authentic sample of (6S)-5,10-dideaza5,6,7,8-tetrahydrofolic acid by HPLC methods A and C.

EXAMPLE 7

(6R)-5,10-dideaza-5,6,7,8-tetrahydrofolic acid

To a suspension of 7.0 g of (6R)-2-amino-4hydroxy-6-[2-(4-carboxyphenyl)ethyl]-5,6,7,8-tetrahydropyrido 2,3-d]pyrimidine hydrochloride and 4.0 g of N-methylmorpholine in 70 ml of dimethylformamide was added 3.5 g of 2-chloro-4,6-dimethoxy-1,3,5-triazine. The mixture was stirred for 20 minutes at ambient temperature, and then 2.1 g of additional N-methylmorpholine and 5.0 g of L-glutamic acid diethyl ester hydrochloride were added. The mixture was stirred for 20 minutes more, and was then filtered and concentrated under vacuum. The residue was triturated with saturated sodium bicarbonate solution and then with water, and then was dried under vacuum. The solids were dissolved in 100 ml of 1N sodium hydroxide and the product was precipitated by the addition of 120 ml of ethanol followed by acidification to pH 3.6. The resulting precipitate was separated by filtration and air dried to obtain 6.9 g of the desired product, identical with an authentic sample by $^1$H NMR and HPLC by methods A and C.

The following series of preparations and Example 8 below illustrate the method of converting the R-product of Example 1 to the corresponding S-compound in order to proceed to the synthesis of (6R)-5,10-dideaza-5,6,7,8-tetrahydrofolic acid.

PREPARATION 2

(S)-4-(4-bromophenyl)-2-[(1,1-dimethylethyl)dimethylsilyloxymethyl]butanol

One g of the product of Example 1 above and 0.5 g of t-butyldimethylsilyl chloride were dissolved in 15 ml of dichloromethane, and 0.22 g of imidazole was added. The mixture was stirred for 20 minutes, while a thick white precipitate formed. The mixture was filtered, was washed with 0.5M hydrochloric acid and dried with sodium sulfate, and was concentrated under vacuum. The residue was purified by bulb-to-bulb distillation to obtain 1.2 g of (S)-4-(4-bromophenyl)-2-[(1,1-dimethylethyl)dimethylsilyloxymethyl]butyl acetate.

bp 210° C. (0.03 mm); $[\alpha]_{589}-0.85°$, $[\alpha]_{365}+1.49°$ (c 0.8, CHCl$_3$); TLC (1:4 ethyl acetate:hexane, silica) R$_f$ 0.57; $^1$H NMR δ 7.39 (d, J=8.3 Hz, 2H), 7.05 (d, J 8.3 Hz, 2H), 4.08 (d, J=6.0 Hz, 2H), 3.60 (d, J=5.2 Hz, 2H), 2.61 (t, J=8.0 Hz, 2H), 2.04 (s, 3H), 1.85 (m, 1H), 1.64 (m, 2H), 0.88 (s, 9H), 0.036 (s, 6H); $^{13}$C NMR δ 170.53, 141.09, 131.33, 129.94, 119.46, 64.35, 62.52, 39.79, 32.55, 29.55, 25.79, 20.64, 18.14, −5.61; IR (CHCl$_3$) 2951, 2922, 2848, 1728, 1485, 1471, 1254, 839 cm$^{-1}$; MS (EI) m/z 414 (1), 225 (20), 223 (22), 171 (19), 169 (18), 144 (26), 117 (100), 75 (64); UV (EtOH) 221 nm (ε=10300), 268 nm (ε=348), 276 nm (ε=245).

Analysis Calculated for C$_{19}$H$_{31}$BrO$_3$Si:
C, 54.93; H, 7.52
Found: C, 55.20; H, 7.31.

A 1.0 g portion of the above intermediate was dissolved in 5 ml of methanol and 4 ml of 1N sodium hydroxide was added. The mixture was rapidly stirred for three hours at ambient temperature, and 20 ml of ethyl acetate was added. The organic phase was separated and was washed twice with saturated sodium chloride, dried with sodium sulfate and concentrated under vacuum. The residue was purified by flash chromatography on 50 g of silica gel, eluting with 1:4 ethyl acetate:hexane to obtain 714 mg of the desired product as an oil.

$[\alpha]_{589}-5.57°$, $[\alpha]_{365}-17.36°$ (c 0.8, CHCl$_3$); TLC (1:4 ethyl acetate:hexane, silica) R$_f$ 0.32; $^1$H NMR δ 7.35 (d, J=8.3 Hz, 2H), 7.03 (d, J=8.3 Hz, 2H), 3.79−3.60 (m, 4H), 3.05 (s, 1H), 2.58 (t, J=7.3 Hz, 2H), 1.70 (m, 1H), 1.56 (m, 2H), 0.89 (s, 9H), 0.065 (s, 6H); $^{13}$C NMR δ 141.28, 131.25, 129.93, 119.37, 65.89, 65.18, 41.60, 32.74, 29.22, 25.76, 18.04, −5.47; IR (CHCl$_3$) 2954, 2930, 2898, 2859, 1488, 1471, 1258, 837 cm$^{-1}$; MS (EI), m/z 373 (1), 225 (28), 223 (27), 171 (30), 169 (33), 144 (55), 129 (16), 105 (25), 75 (100); UV (EtOH) 221 nm (ε=11500), 269 nm (ε=338), 276 nm (ε=249).

Analysis Calculated for C$_{17}$H$_{29}$BrO$_2$Si:
C, 54.68; H, 7.83
Found: C, 54.48; H, 7.77.

PREPARATION 3

(S)-1-azido-4-(4-bromophenyl)-2-[(1,1-dimethylethyl)-dimethylsilyloxymethyl]butane A 578 mg portion of the product of Preparation 2 and 177 mg of methanesulfonyl chloride were dissolved in 3 ml of dichloromethane and cooled to 0°. To the solution was added dropwise 156 mg of triethylamine in 1 ml of dichloromethane. The cooling bath was then removed, and the mixture was stirred for 35 minutes while it warmed to ambient temperature. Three ml of 1M hydrochloric acid was then added, the phases were separated, and the organic phase was dried with sodium sulfate and concentrated under vacuum. The residue was purified by flash chromatography on 75 g of silica gel, eluting with 1:4 ethyl acetate:hexane to obtain 596 mg of (R)-4-(4-bromophenyl)-2-[(1,1-dimethylethyl)-dimethylsilyloxymethyl]butanol methanesulfonate.

$[\alpha]_{589}-4.20°$, $[\alpha]_{365}-12.59°$ (c 0.8, CHCl$_3$); TLC (1:4 ethyl acetate:hexane, silica) R$_f$0.41; $^1$H NMR δ 7.39 d, J=8.3 Hz, 2H), 7.04 (d, J=8.3 Hz, 2H), 4.26 (dd, J=6.0, 9.6 Hz, 1H), 4.24 (dd, J=5.1 9.6 Hz, 1H), 3.65 (dd, J=4.4, 10.2 Hz, 1H), 3.58 (dd, J=6.1, 10.2 Hz, 2H), 2.98 (s, 3H), 2.62 (t, J=8.0 Hz, 2H), 1.89 (m, 2H), 1.65 (m, 2H), 0.89 (s, 9H), 0.056 (s, 6H); $^{13}$C NMR δ 140.60, 131.46, 129.99, 119.67, 69.70, 61.61, 40.20, 37.03, 32.39, 28.90, 25.81, 18.17, −5.55; IR (CHCl$_3$) 2957, 2933, 2860, 1489, 1474, 1360, 838 cm$^{-1}$; MS (EI), m/z 225 (38), 223 (43), 171 (28), 169 (27), 153 (100), 144 (48), 129 (13), 75 (39); UV (EtOH) 221 nm (ε=10500), 268 nm (ε=257), 276 nm (ε=174).

Analysis Calculated for C$_{18}$H$_{31}$BrO$_4$SSi:
C, 47.89; H, 6.92
Found: C, 48.16; H, 6.70.

A 422 mg portion of the above intermediate and 66 mg of sodium azide were dissolved in 5 ml of dimethylformamide and the solution was stirred at 75° for four hours. It was then cooled, and 10 ml of ethyl acetate and 10 ml of water were added. The phases were separated, and the organic phase was washed with saturated sodium chloride solution, dried with sodium sulfate and concentrated under vacuum. The residue was purified by spinning plate thin layer chromatography on a 2 mm silica gel plate with 1:4 ethyl acetate: hexane to obtain 328 mg of the desired product as an oil.

$[\alpha]_{589}-2.98°$, [60 ]$_{365}-15.62°$ (c 0.8, CHCl$_3$); TLC (1:4 ethyl acetate:hexane, silica) R$_f$0.75; $^1$H NMR δ 7.40 (d, J=8.3 Hz, 2H), 7.06 (d, J=8.3 Hz, 2H), 3.64 (dd, J=4.1, 10.1 Hz, 1H), 3.57 (dd, J=5.6, 10.1 Hz, 1H), 3.41 (dd, J=5.9, 12.0 Hz, 1H), 3.37 (dd, J=5.3, 12.0 Hz, 1H), 2.61 (t, J=7.9 Hz, 2H), 1.71 (m, 1H), 1.63 (m, 2H), 0.92 (s, 9H), 0.078 (s, 6H); $^{13}$C NMR δ 141.00, 131.53, 130.02, 119.70, 62.82, 52.64, 40.70, 32.69, 30.29, 25.91, 18.28, −5.49; IR (CHCl$_3$) 2953, 2930, 2858, 2101, 1488, 838 cm$^{-1}$; MS (EI), m/z 341 (4), 339 (4), 284 (9), 282 (9), 171 (28), 169 (28), 130 (100), 75 (52), 59 (41), 73 (34); UV (EtOH) 221 nm (ε=11500), 268 nm (ε=329), 276 nm (ε=242).

Analysis Calculated for C$_{17}$H$_{28}$BrN$_3$OSi:

C, 51.25; H, 7.08; N, 10.55
Found: C, 51.48; H, 7.11; N, 10.70

EXAMPLE 8

(S)-2-azidomethyl-4-(4-bromophenyl)butanol

A 243 mg portion of the product of Preparation 3 was combined with 3 ml of glacial acetic acid, 0.5 ml of tetrahydrofuran and 1.5 ml of water, and the mixture was stirred at 45° for three hours. Then 10 ml of ethyl acetate and 10 ml of 6N sodium hydroxide solution were added, and the organic phase was separated, washed with saturated sodium chloride solution, dried with sodium sulfate and concentrated under vacuum. The residue was purified by spinning plate thin layer chromatography on a 1 mm silica gel plate, with 2:3 ethyl acetate:hexane, to obtain 124 mg of the desired product as an oil. The 1-naphthyl carbamate derivative of a small portion of the product was made, and was analyzed by HPLC, method B, to determine that the product was 95% S-isomer and 5% R-isomer.

$[\alpha]_{589} -0.75°$, $[\alpha]_{365} -2.99°$ (c 0.8, CHCl$_3$); HPLC Method A $t_R$: 4.0 min; Method B: $t_R$: R 15.5 min., S 10.8 min.; TLC (1:1 ethyl acetate:hexane, silica) R$_f$ 0.40; $^1$H NMR δ 7.39 (d, J=8.3 Hz, 2H), 7.04 (d, J=8.3 Hz, 2H), 3.66 (dd, J=4.4, 10.8 Hz, 1H), 3.59 (dd, J=6.1, 10.8 Hz, 1H), 3.45 (dd, J=5.1, 12.2 Hz, 1H), 3.41 (dd, J=6.0, 12.2 Hz, 1H), 2.61 (t, J=7.9 Hz, 2H), 1.93 (s, 1H), 1.76 (m, 1H), 1.65 (m, 2H); IR (CHCl$_3$) 3625, 2930, 2102, 1480 cm$^{-1}$; MS (EI), m/z 256 (7), 254 (4), 226 (16), 224 (18), 199 (39), 198 (62), 197 (37), 196 (60), 171 (76), 169 (75), 130 (27), 129 (26), 90 (100); UV (EtOH) 221 nm (ε=11300), 268 nm (ε=368), 276 nm (ε=280).

Analysis Calculated for C$_{11}$H$_{14}$BrN$_3$O:
C, 46.50; H, 4.97; N, 14.79
Found: C, 46.20; H, 5.04; N, 14.72.

We claim:

1. A compound of the formula

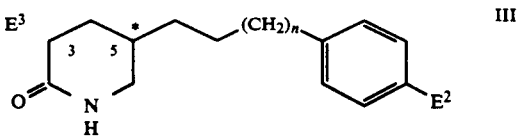

wherein

E$^3$ is cyano or C$_1$-C$_3$ alkoxycarbonyl;

E$^2$ is bromo, chloro, iodo, carboxy, C$_4$-C$_6$ tert-alkoxycarbonyl, cyano, C$_1$-C$_3$ alkylaminocarbonyl, di(C$_1$-C$_3$ alkyl)aminocarbonyl, or [(tetra or penta)methylene]aminocarbonyl;

n is 0 or 1;

and the carbon marked * is in the R or S configuration.

2. A compound of claim 1 wherein E$^3$ is C$_1$-C$_3$ alkoxycarbonyl.

3. A compound of claim 1 wherein the 5-position is in the R conformation.

4. A compound of claim 3 where n is 0.

* * * * *